United States Patent [19]
Roeschert et al.

[11] Patent Number: 5,736,297
[45] Date of Patent: Apr. 7, 1998

[54] POSITIVE-WORKING RADIATION-SENSITIVE MIXTURE AND RECORDING MATERIAL PRODUCED THEREWITH

[75] Inventors: Horst Roeschert, Ober-Hilbersheim; Georg Pawloski, Wiesbaden, both of Germany

[73] Assignee: Clariant GmbH, Frankfurt, Germany

[21] Appl. No.: 681,081

[22] Filed: Jul. 22, 1996

Related U.S. Application Data

[63] Continuation of Ser. No. 195,425, Feb. 14, 1994, abandoned.

[30] Foreign Application Priority Data

Feb. 27, 1993 [DE] Germany ............... 43 06 152.4

[51] Int. Cl.$^6$ .................................. G03C 1/73
[52] U.S. Cl. ............ 430/270.1; 430/326; 430/921; 430/925; 430/919
[58] Field of Search ............... 430/270.1, 326, 430/921, 925, 919

[56] References Cited

U.S. PATENT DOCUMENTS

| | | | |
|---|---|---|---|
| 4,387,152 | 6/1983 | Stahlhofen | 430/280 |
| 4,690,882 | 9/1987 | Tanigaki et al. | 430/270.1 |
| 4,840,867 | 6/1989 | Elsaesser et al. | |
| 5,364,734 | 11/1994 | Pawloski et al. | 430/191 |

FOREIGN PATENT DOCUMENTS

| | | |
|---|---|---|
| 2066148 | 10/1992 | Canada. |
| 0508174 | 10/1992 | European Pat. Off.. |
| 0510441 | 10/1992 | European Pat. Off.. |
| 0519299 | 12/1992 | European Pat. Off.. |
| 3144656 A1 | 7/1982 | Germany. |
| 3930086 | 3/1991 | Germany. |
| 3930087 | 3/1991 | Germany. |
| 4111060 | 10/1991 | Germany. |
| 3223864 | 10/1992 | Japan. |
| 1053866 | 1/1967 | United Kingdom. |

OTHER PUBLICATIONS

Tsunooka et al, Mcintosh et al, Tetrahedron Letters 1967, 37.
Langler et al, Can. J. Chem 65 [1978]903–907.
Ueno et al, Chem. Amplification Positive Resist System Using Novel Sulfonates as Acid Generators, in: "Polymers for Micro–electronic–Science & Tech.", Hrsg. Y. Tabata et al, Kodansha–Weinheim–New York, 1989.
Houlihan et al, SPIE Proc., Adv. in Resit Techn. and Proc. 920 (1988) 67.
Roschert et al, Proceed. SPIE, Adv. Res. Tecn. Process. IX, 1672 [1992]33.
Tsunooka et al, J. Photopolym. Sci. Tech. 4 [1991]239–242.

Primary Examiner—George F. Lesmes
Assistant Examiner—Laura Wener
Attorney, Agent, or Firm—John M. Genova; Andrew F. Sayko, Jr.

[57] ABSTRACT

The invention relates to a positive-working radiation-sensitive mixture containing a) a compound which forms acid when exposed to actinic radiation, b) a compound containing at least one C—O—C or C—O—Si bond which can be cleaved by said acid, and c) a water-insoluble polymeric binder which is soluble, or at least swellable, in aqueous alkaline solutions, wherein the compound a) comprises the structure of the formulae I, II or III:

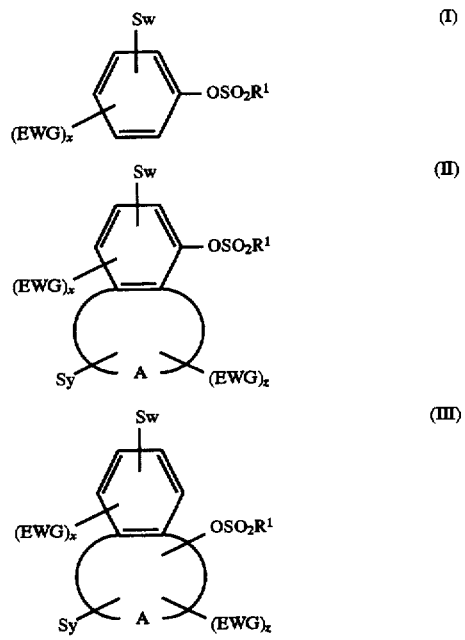

The radiation-sensitive mixture according to the invention is notable for a high resolution and a high sensitivity over a wide spectral range. It also has high thermal stability and does not form any corrosive photolysis products on exposure to light.

The invention furthermore relates to a radiation-sensitive recording material produced therefrom which is suitable for producing photoresists, electronic components, printed circuit boards or for chemical milling.

26 Claims, No Drawings

POSITIVE-WORKING RADIATION-SENSITIVE MIXTURE AND RECORDING MATERIAL PRODUCED THEREWITH

This is a Continuation of application Ser. No. 08/195,425 filed on Feb. 14, 1994, now abandoned.

The invention relates to a positive-working radiation-sensitive mixture containing:

a) a compound which forms a strong acid when exposed to radiation;

b) a compound containing at least one acid-cleavable C—O—C or C—O—Si bond; and c) a water-insoluble binder which is soluble, or at least swellable, in aqueous alkaline solutions;

and to a radiation-sensitive recording material which is produced therewith and is suitable for photoresists and electronic components.

As compounds which form a strong acid on irradiation, use has hitherto been made of, in particular, onium salts, such as diazonium, phosphonium, sulfonium and iodonium salts of nonnucleophilic acids such as $HSbF_6$, $HAsF_6$ or $HPF_6$. In addition, halogen compounds, in particular trichloromethyltriazenes or trichloromethyloxadiazole derivatives, o-naphthoquinonediazidesulfonyl chloride, o-naphthoquinonediazide-4-sulfonic acid esters or oxime sulfonates, have been recommended. These compounds are used in negative- or positive-working radiation-sensitive mixtures. The use of such photolytic acid formers entails, however, certain disadvantages which limit their application possibilities in various fields of application. Thus, for example, numerous onium salts are toxic. Their solubility in many solvents is inadequate, as a result of which only a few solvents are suitable for producing a coating solution. In addition, foreign atoms, some of which are undesirable and which may result in process faults, in particular in microlithography, are introduced if onium salts are used. Furthermore, just like the abovementioned halogen compounds and the quinonediazidesulfonyl chlorides, the onium salts form Brønsted acids having strongly corrosive action during the photolysis. These acids attack sensitive substrates, so that the use of such mixtures leads to unsatisfactory results. The said acid formers have, in addition, only limited stability on certain substrates. In order to increase the stability, an interlayer was inserted between the substrate and the radiation-sensitive layer containing the compounds of type (a). This again led to an increase in defects and to reduced reproducibility (DE-A 36 21 376 =U.S. Pat. No 4,840,867).

In certain acid-labile resist formulations, nitrobenzyl tosylates [F. M. Houlihan et al., SPIE Proc., Adv. in Resist Techn. and Proc. 920 (1988), 67], disulfones of the formula R—$SO_2$—$SO_2$—R' (DE-A 41 11 060), bis(sulfonyl)diazomethane (DE-A 39 30 086) or sulfonylcarbonyldiazomethanes (DE-A 39 30 087) were used. On exposure to light, these compounds form sulfonic acids having no corrosive action or only a low corrosive action and having no migration tendency. The sensitivities thereby achieved and the thermostability of the photoresists do not, however, meet the requirements.

Resist formulations containing these compounds absorb radiation of the wavelength 248 nm to an appreciable extent. The sensitivity to radiation of this wavelength is in the range from 50 to 100 mJ/cm$^2$. Practical patterns having an order of magnitude of 0.5 µm and less cannot be imaged with such resists.

In addition to the inadequate thermostability and the undesirably high absorption in the UV range, a further disadvantage is the poor solubility in many of the solvents normally used.

Similar remarks also apply to β-ketosulfones, which yield sulfinic or sulfonic acids on irradiation (Tsunooka et al., J. Photopolym. Sci. Tech. 4 [1991] 239–242; Tsunooka et al.; McIntosh et al.,Tetrahedron Letters 1967, 37) and to benzyl-substituted β-disulfone compounds (Langler et al., Can. J. Chem. 65 [1978] 903–907).

It is furthermore known to use 1,2,3-Trihydroxybenzene completely esterified with methane-, ethane-, propane-, butane-, benzene-, toluene- or naphthalenesulfonic acid as photoactive acid formers in positive-working photoresist systems (T. Ueno et al., Chemical Amplification Positive Resist Systems Using Novel Sulfonates as Acid Generators, in: "Polymers for Microelectronics—Science and Technology", Editor Y. Tabata et al., Kodansha-Weinheim-New York, 1989, pages 66–67). These resist systems are not, however, used in practice since thermostability and plasma etching resistance are inadequate and resist residues in the trenches and unacceptable resist profiles are to be observed after development.

Sulfonic acid esters of mono-, di- or trihydroxybenzenes and ($C_1$–$C_8$) alkanesulfonic acids, ($C_1$–$C_8$) haloalkanesulfonic acids or ($C_6$–$C_{18}$) arylsulfonic acids are also used in EP-A 0 508 174 as acid formers in a positive-working, chemically fortified resist mixture. The hydroxybenzenes may be substituted with alkyl, alkoxy, phenoxy, phenylmercapto or benzyl groups, that is to say electron-donating groups.

JP-A 03 223 864 discloses a resist material which contains an ester of a mono-, di-, tri- or tetrahydroxybenzene or of a binuclear aromatic compound containing 2 to 8 phenolic hydroxyl groups and 2-nitrobenzenesulfonic acid as acid-forming component.

The multifunctional sulfonic esters described in EP-A 0 510 441 and by T. Ueno (loc. cit.) are only acceptable if the sulfonic acids used for their production have only low absorption. Alkanesulfonic acids were therefore preferably used to esterify the polyhydroxybenzenes. The alkanesulfonic acids liberated from such sulfonic acid esters on irradiation exhibit, however, a relatively high diffusion velocity in the photoresist layer, which leads to a decrease in the line width with increasing waiting time between imagewise irradiation and post-exposure bake (Röschert et al., Proceed. SPIE, Adv. Res. Technol. Process. IX, 1672 [1992] 33).

Despite the intensive research activity hitherto carried out in this field, no radiation-sensitive mixture is at present known which enables a practical positive-working radiation-sensitive recording material to be produced, which has a high sensitivity in the DUV range (200 to 300 nm) and a high resolution, which liberates, even with brief irradiation, a sufficient quantity of an acid which does not have corrosive action and which is strong enough to cleave compounds of the type b) and which can, in addition, also be developed in aqueous alkaline solutions.

The object of the present invention was therefore to propose a radiation-sensitive mixture based on acid-forming compounds in combination with acid-cleavable compounds, the intention being that the compound (a) which forms an acid photolytically should be as stable as possible on all the known substrates and yield an acid which does not have corrosive action as photoproduct.

This object is achieved by a positive-working radiation-sensitive mixture comprising:

a) a compound which forms acid when exposed to actinic radiation;

b) a compound containing at least one C—O—C or C—O—Si bond which can be cleaved by said acid;

c) a water-insoluble polymeric binder which is soluble, or at least swellable, in aqueous alkaline solutions;

wherein the compound (a) comprises the structure of the formulae I, II or III

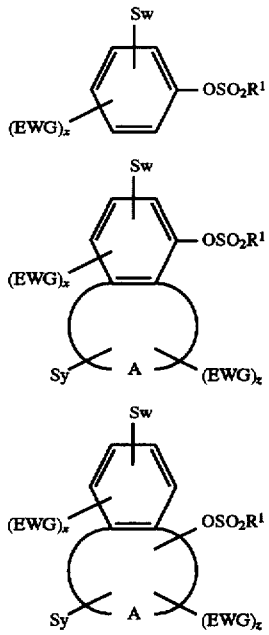

in which

S is an unsubstituted or substituted acyclic, isocyclic or heterocyclic radical containing 1 to 20 carbon atoms, EWG is an electron-withdrawing group, $R^1$ is an unsubstituted or substituted acyclic, isocyclic or heterocyclic radical containing 1 to 20 carbon atoms, A is the residual ring members necessary to form a 5- to 7- member saturated or unsaturated isocyclic or heterocyclic ring, the hetero atoms in the heterocyclic ring being oxygen, sulphur and/or nonbasic nitrogen atoms, w and y are, independently of one another, 0, 1 or 2, x is an integer from 1 to 5 in the compounds of the formula I, an integer from 1 to 3 in the compounds of the formulae II and III, z is an integer from 1 to 4 in the compounds of the formula II, and an integer from 1 to 3 in the compounds of the formula III.

Radical S, which is only optionally present, is, in particular, methyl, ethyl, propyl, isopropyl, butyl, sec-butyl, isobutyl, tert-butyl, formyl, acetyl, methoxycarbonyl, phenyl, benzyl, cyclohexyl, benzoyl, phenethyl, 3-phenylpropyl, 1-naphthyl or 2-naphthyl. If the radical S is heterocyclic, it has, in addition to 4 to 9 carbon atoms, also an oxygen or sulphur atom, or 1 or 2 nitrogen atoms in the heterocyclic ring system. Examples of this are furyl, thienyl, pyrrolyl, pyridinyl and quinolinyl radicals. Again, the nitrogen-containing heterocyclics must not be basic. The radicals S may be substituted in the same way as the radicals $R^1$. In addition, they may also be substituted by hydroxy and sulfonyloxy (—O—$SO_2$—$R^1$, where $R^1$ has the abovementioned meaning). The aromatic radicals S are preferably substituted by ($C_1$–$C_4$)alkoxy, ($C_1$–$C_8$)alkanoyl, sulfonyloxy (—O—$SO_2$—$R^1$) or halogen. If a plurality of substituents is bound to one aromatic radical, they are preferably selected from the group comprising ($C_1$–$C_4$)alkyl, hydroxy, sulfonyloxy (—O—$SO_2$—$R^1$) and halogen. Particularly preferably S is a ($C_1$–$C_4$)alkyl group.

Particularly suitable electron-withdrawing groups EWG are fluorine, chlorine or bromine atoms, cyano, formyl, 2,2,2-trifluoroethyl, 2,2,2-trifluoro-1-hydroxy-1-trifluoromethylethyl=[—C($CF_3$)$_2$—OH], perfluoro($C_1$–$C_{10}$) alkyl, (in particular trifluoromethyl), trichloromethyl and tribromomethyl, perfluoro($C_1$–$C_{10}$)alkoxy, (in particular trifluoromethoxy), trichloromethoxy, trihalomethanesulfonyl and dicyanomethyl and 2,2-dicyanovinyl groups. Also equally suitable are groups of the formulae —$SO_2$—$R^2$, —CO—$R^3$ and —O—CO—$R^4$, where $R^2$ to $R^4$ have the following meanings:

$R^2$ and $R^3$ are ($C_1$–$C_{10}$) alkyl, ($C_3$–$C_7$) cycloalkyl, ($C_6$–$C_{14}$) aryl or ($C_7$–$C_{20}$) aralkyl, and $R^4$ is one of the radicals specified for $R^2$, or ($C_1$–$C_{10}$) alkoxy.

The action of the EWG group can also be transmitted by one or more double bond(s) (vinylogy principle).

Particularly suitable $R^1$ radicals are methyl, ethyl, propyl, isopropyl, butyl, sec-butyl, isobutyl, tert-butyl, pentyl, hexyl and octyl groups, and in addition, also cyclohexyl, phenyl, benzyl, phenethyl, 3-phenylpropyl and 1-naphthyl and 2-naphthyl groups. The radicals $R^1$ may also be heteroaromatic. Preferably, they then have, in addition to 4 to 9 carbon atoms, also an aromatic oxygen or sulphur atom, or 1 or 2 aromatic nitrogen atoms. Examples of this are 2-furyl or 3-furyl, 2-thienyl or 3-thienyl, 1-pyrrolyl, 2-pyrrolyl or 3-pyrrolyl, pyridyl, pyrimidinyl and pyrazinyl radicals. Binuclear heteroaryl radicals are also suitable. For these, mention may be made of the benzofuryl, isobenzofuryl, benzo[b]thienyl, benzo[d][1,3]thiazolyl, benzo[c][1,2,5] oxadiazolyl (=benzofurazanyl) and indolyl radicals. The nitrogen-containing heterocyclics must not, however, be basic.

The radical $R^1$ may be substituted still further. In principle, all those substituents, which do not enter into any undesirable reactions may occur. Suitable substituents are linear and branched alkyl groups containing, preferably, not more then 8 carbon atoms, in particular not more than 6 carbon atoms, such as methyl, ethyl, propyl, isopropyl, butyl, sec-butyl, isobutyl and tert-butyl. The alkyl groups may be fluorinated, and preferably perfluorinated. Of the perfluorinated alkyl radicals, trifluoromethyl and perfluorobutyl are particularly suitable. Further suitable substituents are ($C_1$–$C_8$)alkoxy, ($C_1$–$C_8$)alkoxy($C_1$–$C_8$)alkoxy, ($C_1$–$C_8$)alkanoyl, ($C_1$–$C_8$)alkanoyloxy, ($C_1$–$C_8$) alkanoylamino, ($C_6$–$C_{10}$)aryl, ($C_6$–$C_{10}$)aryloxy, ($C_6$–$C_{10}$) aryl ($C_1$–$C_8$)alkoxy, ($C_6$–$C_{11}$)aroylamino, ($C_6$–$C_{11}$) aroylamino ($C_1$–$C_6$)alkyl, cyano and halogen. The substituents may occur repeatedly. Independently of this, various substituents may be present alongside one another. Preferred substituents are ($C_1$–$C_4$)alkyl, ($C_1$–$C_4$)alkoxy and phenyl. The phenyl radical is in turn preferably substituted by ($C_1$–$C_6$)alkyl, ($C_1$–$C_8$)perfluoroalkyl and/or halogen, in particular fluorine. Preferably, one of these substituents of the phenyl radical is in the p- position. Nitro groups do not occur in the compounds of the formulae I to III since they would reduce the efficiency of the acid formation.

These compounds provide acids, predominantly sulfonic acids, with a high quantum yield and are, in addition, sufficiently thermally stable.

The sulfonic acid esters of the formulae I to III can be prepared by methods which are known per se to the person skilled in the art. The simplest way of doing this is to react the corresponding phenols (or compounds containing phenolic hydroxyl groups) with sulfonyl chlorides in the presence of a sufficiently strong base. Preferred in this connection are phenols and, in general, compounds containing phenolic hydroxyl groups and whose $pK_a$ is in each case less than 10.

Examples of particularly suitable sulfonyl chlorides are camphor-10-sulfonyl chloride, 1-naphthalene- and 2-naphthalensulfonyl chloride, 1,2,3,4-tetrahydronaphthalene-5-sulfonyl chloride, 6,7-bismethane-sulfonyloxynaphthalene-2-sulfonyl chloride, 4-pentylbenzenesulfonyl chloride, 1,2-naphthoquinone-2-diazide-4- and -5-sulfonyl chloride, 5-benzenesulfonylthiophen-2-sulfonyl chloride and benzo[d][1,2,5]-oxadiazole-4-sulfonyl chloride. Compounds containing more than one sulfonyl chloride group are also suitable. Of the bifunctional sulfonyl chlorides, mention should be made in particular of benzene-1,3-disulfonyl chloride and oxybiphenyl-4,4'-disulfonyl chloride and of the polyfunctional poly(4-chlorosulfonylstyrene) and poly(2-chlorosulfonylstyrene).

It was surprising that the compounds of the formulae I, II and III used in the mixtures according to the invention provide adequate amounts of sufficiently strong acids on exposure to radiation. It was particularly surprising that they also provide acid to a sufficient extent, even on exposure to UV-2 radiation, in particular to radiation having a wavelength of 248 nm since it was known that most of the representatives of this category of compounds absorb only to a slight extent in this wavelength range (the absorption coefficient $\epsilon$ at 248 nm is less than 10,000 1 mol$^{-1}$ cm$^{-1}$ for almost all the compounds).

The radiation-sensitive mixture according to the invention is remarkable for its high sensitivity. It exhibits a high thermostabilty and provides the possibility of reproducing even the finest patterns of am aster with precise definition of details. The acid formed during the irradiation does not have corrosive action, with the result that the mixture can also be used for sensitive substrate materials.

In particular, UV radiation in the range from 190 to 260 nm, preferably from 200 to 250 nm, and also electron or X-ray radiation are suitable for the imagewise irradiation.

The mixture according to the invention may also contain various compounds of the formulae I, II and III as acid formers. In addition, other acid formers may also be used. Such additional acid formers are, for example, the multifunctional sulfonic acid esters of 2,4,6-tris-(2-hydroxyethoxy)-[1,3,5]-triazine described in DE-A 41 12 971. In addition, 1,2-diasulfones, bis(sulfonyl) diazomethane and sulfonylcarbonyldiazomethanes are suitable. Mixtures containing such additional acid formers are, however, not preferred.

The proportion of acid-forming compounds in total and that of compounds of the formulae I, II and III in the mixture according to the invention are in general about 0.25 to about 25% by weight, preferably about 0.5 to about 10% by weight, based in all cases on the total weight of the non-volatile constituents of the mixture.

As acid-cleavable compounds b) in the radiation-sensitive mixture according to the invention, those from one of the following categories of compounds, in particular, have been found satisfactory.

a) Compounds containing at least one ortho-carboxylic ester group and/or carboxylic acid amid acetal group, it being possible for the compounds also to have a polymeric nature and for the groups mentioned to occur in the main chain or laterally, b) oligomeric or polymeric compounds containing repeating acetal and/or ketal groups in the main chain, c) compounds containing at least one enol ether or N-acylaminocarbonate group, d) cyclic acetals or ketals of β-keto esters or β-keto amides, e) compounds containing silyl ether groups, f) compounds containing silyl enol ether groups, g) monoacetals or monoketals of aldehydes or ketones whose solubility in the developer is between 0.1 and 100 g/l, h) ethers derived from tertiary alcohols, i) carboxylic esters and carbonates whose alcohol component is a tertiary alcohol, an allyl alcohol or a benzyl alcohol, and j) N,O-acetals, in particular N,O-polyacetals.

Mixtures of the abovementioned acid-cleavable compounds may also be used. Of the compounds mentioned, those containing at least one acid-cleavable C—O—C bond, in particular, are preferred, i.e. the compounds of categories a), b), g) and i) and j). Of type b), the polymeric acetals should be particularly highlighted; of the acid-cleavable materials of type g), in particular those should be highlighted which are derived from aldehydes or ketones having a boiling point above 150° C., preferably above 200° C. Mixtures containing various acid-cleavable compounds are generally not preferred.

The proportion of the compound(s) b) is generally about 1 to about 50% by weight, preferably about 10 to about 40% by weight, based in all cases on the total weight of the solids in the radiation-sensitive mixture.

The radiation-sensitive mixture according to the invention furthermore contains at least one polymeric water-insoluble binder c) which is soluble, or at least swellable, in aqueous alkaline solutions. The binder is notable, in particular, for the fact that it has good compatibility with the other constituents of the radiation-sensitive mixture according to the invention and, in particular, has as low a self-absorption as possible in the wavelength range from 190 to 300 nm, i.e. a high transparency. Binders based on novolak condensation resins, which are usually used in combination with naphthoquinone diazides as photoactive components, do not fulfil this requirement. Although novolak condensation resins exhibit a reduction in the solubility with respect to aqueous alkaline developers in the unexposed regions after imagewise exposure to light, their self-absorption in the region of the short wavelength required for the irradiation is undesirably high.

Novolak condensation resins may, however, be used when mixed with other resins which are suitable as binders and have high transparency. In this connection, the mixing ratios predominantly depend on the type of binder to be mixed with the novolak. In particular, its degree of self-absorption in the wavelength range mentioned and also its miscibility with the other constituents of the radiation-sensitive mixture play a decisive role. In general, however, the binder of the radiation-sensitive mixture according to the invention may contain up to about 30% by weight, in particular up to about 20% by weight, of a novolak condensation resin.

Suitable binders are homo- or copolymers of 4-hydroxystyrene and its alkyl derivatives, for example 3-methyl-4-hydroxystyrene, and homo- or copolymers of other vinylphenols, for example of 3-hydroxystyrene or the esters or amides of acrylic acid with aromatics containing phenolic groups. Polymerizable compounds such as styrene, methyl (meth)acrylate or the like can be used as comonomers.

Layers having increased plasma resistance are obtained if silicon-containing binders, for example composed of vinyltrimethylsilane, are used therein. The transparency of these binders in the deep UV range is generally higher, with the result that an improved patterning is possible.

Homo- or copolymers of maleimide can also be used with equal success. These binders also have high transparency in the deep UV range. Here styrene, substituted styrenes, vinyl ethers, vinyl esters, vinylsilyl compounds or (meth)acrylic esters are preferably also used as comonomers.

Finally, copolymers of styrene can also be used, in addition, with comonomers which bring about an increase in solubility in aqueous alkaline solutions. These include, for example, maleic anhydride and maleic acid half-esters.

The known binders may also be mixed with one another if the optical quality of the radiation-sensitive mixture does not deteriorate as a result. Binder mixtures are, however, not preferred.

The absorbance of the binder or of the combination of binders for radiation of the wavelength 248 nm is preferably less than 0.35, particularly preferably less than 0.25 $\mu m^1$.

The glass transition temperature of the binder or of the combination of binders is preferably at least 120° C.

The proportion of the binder is generally about 1 to about 98.5% by weight, preferably about 25 to about 90% by weight, particularly preferably about 50 to about 80% by weight, based in all cases on the total weight of the solid components of the radiation-sensitive mixture.

Finally, the mixtures according to the invention may also contain further components such as dyes, pigments, plasticizers, wetting agents and levelling agents. To fulfil special requirements such as flexibility, adhesion and lustre, compounds such as polyglycol, cellulose ethers, for example ethylcellulose, may also be used.

If a substrate is to be coated, the radiation-sensitive mixture according to the invention is expediently dissolved in a solvent or in a combination of solvents. Particularly suitable for this purpose are glycols such as ethylene glycol and propylene glycol and the mono- and dialkyl ethers derived therefrom, particularly the mono-and dimethyl ethers and the mono- and diethyl ethers, esters derived from aliphatic $(C_1-C_6)$carboxylic acids and either $(C_1-C_8)$ alkanols or $(C_1-C_8)$alkanediols or $(C_1-C_6)$alkoxy-$(C_1-C_8)$ alkanols, for example ethyl acetate, hydroxyethyl acetate, alkoxyethyl acetate, n-butyl acetate, propylene glycol monoalkyl ether acetate, in particular propylene glycol methyl ether acetate and amyl acetate, ethers such as tetrahydrofuran and dioxane, ketones such as methyl ethyl ketone, methyl isobutyl ketone, cyclopentanol and cyclohexone, N,N-dialkylcarboxylamides, such as N,N-dimethylformamide and N,N-dimethylacetamide, and also hexamethylphosphoric triamide, N-methyl-2-pyrrolidone and butyrolactone, and also any desired mixtures thereof. Of these, the glycol ethers, aliphatic esters and ketones are particularly preferred.

Ultimately the choice of solvent or solvent mixture depends on the coating method applied, the desired layer thickness and the drying conditions. The solvents must also be chemically inert towards the other layer components under the conditions applied.

The solution prepared with the solvents mentioned usually has a solids content of about 5 to about 60% by weight, preferably about 10 to about 40% by weight.

Finally the invention also relates to a radiation-sensitive recording material which essentially comprises a substrate and a radiation-sensitive layer which is situated thereon and is comprised of the mixture according to the invention.

Suitable substrates are all those materials of which capacitors, semiconductors, multilayer printed circuits or integrated circuits may be composed or from which they may be produced. Specific mention should be made of silicon substrates, which may also be coated by thermal oxidation and/or with aluminum, and may also be doped. In addition, all the other substrates which are usual in semiconductor technology, such as silicon nitride, gallium arsenide and indium phosphide are possible. These substrates may be thermally pretreated, superficially grained, incipiently etched or, to improve desired properties, for example to increase the hydrophilic nature, be treated with chemicals.

In order to impart a better cohesion and/or a better adhesion on the substrate surface to the radiation-sensitive layer, the latter may contain an adhesion promotor. In the case of silicon and silicon dioxide substrates, adhesion promoters of the aminosilane type such as, for example, 3-aminopropyltriethoxysilane or hexamethyldisilazane are suitable for this purpose.

Suitable radiation sources for the imagewise irradiation are particularly metal-halide lamps, carbon-arc lamps, zenon lamps and mercury-vapor lamps. An exposure to high-energy radiation such as laser, electron or x-ray radiation may likewise be carried out. Particularly preferred, however, are lamps which are able to emit light of a wavelength from 190 to 260 nm, i.e. in particular xenon and mercury-vapor lamps. In addition, laser light sources, for example excimer lasers, in particular KrF or ArF lasers which emit at 248 or 193 nm can also be used. The radiation sources must have an adequate emission in the wavelength ranges mentioned.

The thickness of the photosensitive layer depends on the application. It is generally between about 0.1 and about 100 µm, preferably between about 0.5 and about 10 µm, particularly preferably about 1.0 µm.

The radiation-sensitive recording material is expediently produced by applying the radiation-sensitive mixture to the substrate, for example, by spraying-on, flow coating, rolling, spinning and immersion coating. The solvent is then removed by evaporation so that the radiation-sensitive layer remains behind on the surface of the substrate. The removal of the solvent can be promoted by heating the layer to temperatures of up to 150° C. The mixture may, however, also first be applied in the abovementioned manner to an intermediate support from which it is transferred to the final support material under pressure and at elevated temperature. In principle, all the materials which are also suitable as support materials may be used as intermediate support. The layer is then imagewise irradiated. The layer is then treated with a developer solution which dissolves and removes the irradiated regions of the layer, with the result that an image of the master used during the imagewise irradiation remains on the substrate surface.

Suitable developers are particularly aqueous solutions containing silicates, metasilicates, hydroxides, hydrogen- and dihydrogenphosphate, carbonates or hydrogencarbonates of alkali-metal, alkaline-earth-metal and/or ammonium ions, and also ammonia and the like. Metal-ion-free developers are preferred. The content of these substances in the developer solution is generally about 0.1 to about 15% by weight, preferably about 0.5 to about 5% by weight, based on the weight of the developer solution. Small amounts of a wetting agent, which promote the stripping of the soluble regions of the layer may optionally be added to the developers.

The radiation-sensitive mixture according to the invention is used in the production of integrated circuits or of discreet electrical components by lithographic processes since they have a high photosensitivity, particularly when irradiated with light of wavelength between 190 to 300 nm. The developed resist layer then serves as mask for the subsequent process steps. Such steps are, for example, the etching of the layer support, the implantation of ions in the layer support or the deposition of metals or other materials on the layer support.

The examples described below illustrate the invention, but are not intended to have a restricting effect. In these examples, pbw stands for parts by weight.

Example 1

A coating solution was prepared from 25 pbw of a copolymer of 3-methyl-4-hydroxystyrene and 4-hydroxystyrene (molar ratio 1:2) having a mean molecular weight of 18,000 g/mol (GPC), 10.7 pbw of a polyorthoester prepared by condensing 1 mol of 7,7-bishydroxymethyl-1-nonanol with 1 mol of trimethyl orthoformate, and 0.45 pbw of bis(2,4-dicyanophenyl)benzene-1,3-disulfonate in 100 pbw of propylene glycol monomethyl ether acetate.

The coating solution was filtered through a filter having a pore diameter of 0.2 µm and spun onto a wafer, which had been pretreated with an adhesion promotor (hexamethyldisilazane), at a rotary speed of 3,500 rev/min. After drying for 1 min at 120° C. on a hot plate, a layer thickness of 1.00 µm was obtained.

The coated wafer was imagewise irradiated under a master with UV radiation from a xenon/mercury-vapor lamp (248 nm) at a power of 28 mJ/cm$^2$ and then aftertreated thermally for 1 min on a hot plate at 65° C.

Development was then carried out with a 0.16N aqueous tetramethylammonium hydroxide solution. After 60 seconds at 21° C. the irradiated regions were stripped without residue. An image of the master which was faithful to detail was obtained. Lines and trenches were reproduced exactly down to an order of magnitude of less than 1 µm.

Example 2

A wafer coated as in Example 1 was irradiated under a master with the UV radiation of a KrF excimer laser (248 nm) at a power of 29 mJ/cm2. As in the preceding example, an image of the master which was true to the original and in which even patterns of less than 1 µm were resolved was obtained.

Example 3

A coating solution was prepared from 25 pbw of a homopolymer of 3-methyl-4-hydroxystyrene having a mean molecular weight of 26,000 g/mol, 10.7 pbw of a polyacetyl prepared from benzaldehyde and N-butyl-4-hydroxybuteramide having a mean molecular weight of 4,000 g/mol, and 0.5 pbw of 2,5-dichlorophenyl benzo[c][1,2,5]oxadiazole-4-sulfonate in 100 pbw of propylene glycol monomethyl ether acetate.

The coating solution was filtered through a filter having a pore diameter of 0.2 µm and spun at a rotary speed of 3,300 rev/min onto a wafer which had been pretreated with an adhesion promoter (hexamethyldisilazane). After drying for 1 min at 120° C. on a hot plate, a layer thickness of 1.00 µm was obtained.

The coated wafer was imagewise irradiated under a master with the UV radiation from a xenon/mercury-vapor lamp (248 nm) at a power of 40 mJ/cm$^2$ and then aftertreated thermally for 1 min at 55° C.

Development was then carried out with a 0.27N aqueous tetramethylammonium hydroxide solution. After 75 seconds, the irradiated regions had been stripped without residue. An image of the master which was faithful to detail and had rectangular resist edges was obtained. Details having a size of less than 0.5 µm were still reproduced exactly. The dark erosion was less than 20 nm.

Example 4

A coating solution was prepared from 50 pbw of a copolymer of styrene and 4-hydroxystyrene (25/75) having a mean molecular weight of 28,000 [determined by gel permeation chromatography (GPC)], 20 pbw of 4-hydroxy-3-methoxybenzaldehyde bis phenoxyethyl acetyl and 0.7 pbw of 4-trifluoromethylphenyl 1,2,3,4-tetrahydronaphthalene-5-sulfonate in 200 pbw of propylene glycol monomethyl ether acetate.

The coating solution was filtered through a filter having a pore diameter of 0.2 µm and was spun at a rotary speed of 3,200 rev/min onto a wafer which had been pretreated with an adhesion promotor (hexamethyldisilazane). After drying for 1 min at 120° C. on a hot plate, a layer thickness of 1.13 µm was obtained.

The recording material was imagewise irradiated under a master with the UV radiation from a xenon/mercury-vapor lamp (248 nm) at a power of 37 mJ/cm$^2$ and then subjected for 1 min to a post-exposure bake on a hot plate at 70° C.

The recording material was developed with a 0.18N aqueous tetramethylammonium hydroxide solution. After a development time of 50 seconds, a fault-free image of the mask was obtained which had steep resist edges, even patterns of 0.8 µm being resolved faithfully to detail. The scanning electron microscope examination revealed that the edges of the resist profiles were aligned virtually perpendicularly to the substrate surface.

Example 5

A coating solution was prepared from 25 pbw of a copolymer of 3-methyl-4-hydroxystyrene and 4-hydroxystyrene (1:1) having a mean molecular weight of 19,000 g/mol, 10.7 pbw of an N,O-polyacetyl, prepared from benzaldehyde and 2-hydroxyethyl N-propylcarbonate having a mean molecular weight of 6,500 g/mol, and 0.7 pbw of pentafluorophenyl 4-chlorobenzenesulfonate in 100 pbw of propylene glycol monoethyl ether acetate.

The coating solution was filtered through a filter having a pore diameter of 0.2 µm and spun at a rotary speed of 3,700 rev/min onto a wafer which had been pretreated with an adhesion promoter (hexamethyldisilizane). After drying for 1 min at 120° C. on a hot plate, a coating thickness of 1.04 µm was obtained.

The recording material was imagewise irradiated under a master with the UV radiation from a KrF excimer laser (248 nm) with a power of 30 mJ/cm$^2$ and then aftertreated thermally for 1 min at 60° C.

Development was then carried out with a 0.24N aqueous tetramethylammonium hydroxide solution. After 60 seconds, the irradiated regions were stripped without residue. An image of the master which was faithful to detail and had steep resist edges was obtained. The resolution of the lines and trenches was down to 0.35 µm.

Example 6 (comparison example)

The resist formulation of Example 5 was modified so that the acid-forming compound used therein was replaced by the same amount of 1,2,3-tris(4-chlorobenzenesulfonyloxy)benzene.

After irradiation at 248 nm with a power of 32 mJ/cm² and subsequent development in accordance with Example 5, a resist image was obtained which had a reduced resolution (0.5 µm) and, in particular, no patterns suitable for practical purposes, i.e. the resist edges were not vertical.

We claim:

1. A positive-working radiation-sensitive mixture consisting essentially of:
    a) a compound which forms acid when exposed to actinic radiation,
    b) a compound containing at least one C—O—C or C—O—Si bond which can be cleaved by said acid, and
    c) a water-insoluble polymeric binder which is soluble, or at least swellable, in aqueous alkaline solutions, wherein the compound (a) comprises the structure of the formula I

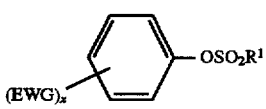

in which
   EWG is an electron-withdrawing group selected from the group consisting of fluorine, chlorine or bromine atom, a cyano, formyl, 2,2,2- trifluoroethyl, 2,2,2-trifluoro-1-hydroxyl-1-trifluoromethylethyl $=[-C(CF_3)_2OH]$ perfluoro($C_1$–$C_{10}$)alkyl, perfluoro($C_1$–$C_{10}$)alkoxy, dicyanomethyl, 2,2-dicyanovinyl groups or a group of the formula $-SO_2-R^2$, $-CO-R^3$ and $-O-CO-R^4$, in which
   $R^2$ and $R^3$ are ($C_1$–$C_{10}$)alkyl, ($C_3$–$C_7$)cycloalkyl, ($C_6$–$C_{14}$)aryl or ($C_7$–$C_{20}$)aralkyl, and
   $R^4$ is one of the radicals specified for $R^2$ or ($C_1$–$C_{10}$) alkoxy,
   $R^1$ is an unsubstituted or substituted acyclic, isocyclic or heterocyclic radical containing 1 to 20 carbon atoms selected from methyl, ethyl, propyl, isopropyl, butyl, sec-butyl, isobutyl, tert-butyl, pentyl, hexyl, octyl, cyclohexyl, phenyl benzyl, phenethyl, 3-phenylpropyl, 1-naphthyl, 2-naphthyl, 1,2-furyl, 3-furyl, 2-thienyl or 3-thienyl, 1-pyrrolyl, 2-pyrrolyl or 3-pyrrolyl, pyridyl pyrimidinyl, pyrazinyl, benzofuryl, isobenzofuryl, benzo[b]thienyl benzo[d][1,3]thiazol, benzo[c][1,2,5]oxadiazolyl (=benzofurazanyl) indolyl, and further substituted $R^1$ groups wherein the further substituents are selected from methyl, ethyl, propyl, isopropyl, butyl, sec-butyl, isobutyl, tert-butyl, trifluoromethyl, perfluorobutyl, ($C_1$–$C_8$)alkoxy, ($C_1$–$C_8$)alkoxy($C_1$–$C_8$) alkoxy, ($C_1$–$C_8$)alkanoyl, ($C_1$–$C_8$)alkanoyloxy, ($C_1$–$C_8$)alkanoylamino, ($C_6$–$C_{10}$)aryl, ($C_6$–$C_{10}$) aryloxy, ($C_6$–$C_{10}$)aryl($C_1$–$C_8$)alkoxy, ($C_6$–$C_{11}$) aroylamino, ($C_6$–$C_{11}$)aroylamino($C_1$–$C_6$)alkyl, cyano, halogen, phenyl and phenyl radical substituted by ($C_1$–$C_6$)alkyl, ($C_1$–$C_8$)perfluoroalkyl and halogen and x is an integer from 1 to 5.

2. The radiation-sensitive mixture as claimed in claim 1, wherein the perfluoro ($C_1$–$C_{10}$) alkyl group is trifluoromethyl.

3. The radiation-sensitive mixture as claimed in claim 1, wherein the perfluoro ($C_1$–$C_{10}$) alkoxy group is trifluoromethoxy.

4. The radiation-sensitive mixture as claimed in claim 1, wherein the radical $R^1$ is a methyl, ethyl, propyl, isopropyl, butyl, sec-butyl, isobutyl, tert-butyl, pentyl, hexyl, octyl, cyclohexyl, phenyl, benzyl, phenethyl, 3-phenylpropyl, 1-naphthyl or 2-naphthyl radical, or a heteroaromatic radical containing 4 to 9 carbon atoms, and one aromatic oxygen or sulphur atom, or one or two aromatic non-basic nitrogen atoms.

5. The radiation-sensitive mixture as claimed in claim 4, wherein the heteroaromatic radical is a 2-furyl or 3-furyl, 2-thienyl or 3-thienyl, 1-pyrrolyl, 2-pyrrolyl or 3-pyrrolyl, pyridyl, pyrimidinyl, pyrazinyl, benzofuryl, isobenzofuryl, benzo[b]thienyl, benzo[d][1,3]thiazolyl, benzo[c][1,2,5] oxadiazolyl (=benzofurazanyl) or indolyl radical.

6. The radiation-sensitive mixture as claimed in claim 1, wherein the proportion of acid-forming compound a) is about 0.25 to about 25% by weight based on the total weight of the nonvolatile constituents in the mixture.

7. The radiation-sensitive mixture as claimed in claim 6, wherein the proportion of acid forming compound is about 0.5 to about 10% by weight based on the total weight of the nonvolatile constituents in the mixture.

8. The radiation-sensitive mixture as claimed in claim 1, wherein the proportion of the compound b) is about 1 to about 50% by weight, based on the total weight of the solids in the radiation-sensitive mixture.

9. The radiation-sensitive mixture as claimed in claim 8, wherein the proportion of the compound b) is about 10 to about 40% by weight based on the total weight of the solids in the radiation-sensitive mixture.

10. The radiation-sensitive mixture as claimed in claim 1, wherein the proportion of the binder c) is about 1 to about 98.5% by weight, based on the total weight of the radiation-sensitive mixture.

11. The radiation-sensitive mixture as claimed in claim 10, wherein the proportion of the binder c) is about 25 to about 90% by weight based on the total weight of the radiation-sensitive mixture.

12. The radiation-sensitive mixture as claimed in claim 11, wherein the proportion of the binder c) is about 50 to about 80% by weight, based on the total weight of the radiation-sensitive mixture.

13. The radiation-sensitive mixture as claimed in claim 1, wherein the mixture contains one or more additives selected from the group consisting of dyes, pigments, plasticizers, wetting agents, levelling agents, polyglycol and cellulose ethers.

14. A positive-working radiation sensitive recording material consisting essentially of a support having a radiation-sensitive layer, wherein the layer is composed of a mixture comprising:
    a) a compound which forms acid when exposed to actinic radiation,
    b) a compound containing at least one C—O—C or C—O—Si bond which can be cleaved by said acid, and
    c) a water-insoluble polymeric binder which is soluble, or at least swellable, in aqueous alkaline solutions, wherein the compound (a) comprises the structure of the formula I

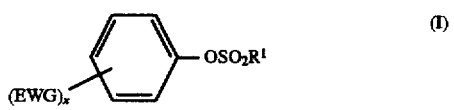

in which
   EWG is an electron-withdrawing group selected from the group consisting of fluorine, chlorine or bromine atom, a cyano, formyl, 2,2,2- trifluoroethyl, 2,2,2-trifluoro-1-hydroxyl-1-trifluoromethylethyl =[—C(CF$_3$)$_2$OH] perfluoro(C$_1$–C$_{10}$)alkyl, perfluoro(C$_1$–C$_{10}$)alkoxy, dicyanomethyl, 2,2-dicyanovinyl groups or a group of the formula —SO$_2$—R$^2$, —CO—R$^3$ and —O—CO—R$^4$, in which R$^2$ and R$^3$ are (C$_1$–C$_{10}$)alkyl, (C$_6$–C$_{14}$)cycloalkyl, (C$_3$–C$_7$)aryl or (C$_7$–C$_{20}$)aralkyl, and R$^4$ is one of the radicals specified for R$^2$ or (C$_1$–C$_{10}$) alkoxy, R$^1$ is an unsubstituted or substituted acyclic, isocyclic or heterocyclic radical containing 1 to 20 carbon atoms selected from methyl, ethyl, propyl, isopropyl, butyl, sec-butyl, isobutyl, tert-butyl, pentyl, hexyl, octyl, cyclohexyl, phenyl, benzyl, phenethyl, 3-phenylpropyl, 1-naphthyl, 2-naphthyl, 2-furyl, 3-furyl, 2-thienyl or 3-thienyl, 1-pyrrolyl, 2-pyrrolyl or 3-pyrrolyl, pyridyl, pyrimidinyl, pyrazinyl, benzofuryl, isobenzofuryl, benzo[b]thienyl, benzo[d][1,3]thiazolyl, benzo[c][1,2,5]oxadiazolyl (=benzofurazanyl), indolyl, and further substituted R$^1$ groups wherein the further substituents are selected from methyl, ethyl, propyl, isopropyl, butyl, sec-butyl, isobutyl, tert-butyl, trifluoromethyl, perfluorobutyl, (C$_1$–C$_8$)alkoxy, (C$_1$–C$_8$)alkoxy(C$_1$–C$_8$) alkoxy, (C$_1$–C$_8$)alkanoyl, (C$_1$–C$_8$)alkanoyloxy, (C$_1$–C$_8$)alkanoylamino, (C$_6$–C$_{10}$)aryl, (C$_6$–C$_{10}$) aryloxy, (C$_6$–C$_{10}$)aryl(C$_1$–C$_8$)alkoxy, (C$_6$–C$_{11}$) arylamino, (C$_6$–C$_{11}$)aroylamino(C$_1$–C$_6$)alkyl, cyano, halogen, phenyl and phenyl radical substituted by (C$_1$–C$_6$)alkyl, (C$_1$–C$_8$)perfluoroalkyl and halogen and x is an integer from 1 to 5.

15. The radiation-sensitive recording material as claimed in claim 14, wherein the perfluoro (C$_1$–C$_{10}$) alkyl group is trifluoromethyl.

16. The radiation-sensitive recording material as claimed in claim 14, wherein the perfluoro (C$_1$–C$_{10}$) alkoxy group is trifluoromethoxy.

17. The radiation-sensitive recording material as claimed in claim 14, wherein the radical R$^1$ is a methyl, ethyl, propyl, isopropyl, butyl, sec-butyl, isobutyl, tert-butyl, pentyl, hexyl, octyl, cyclohexyl, phenyl, benzyl, phenethyl, 3-phenylpropyl, 1-naphthyl or 2-naphthyl radical, or a heteroaromatic radical containing 4 to 9 carbon atoms, and one aromatic oxygen or sulphur atom, or one or two aromatic non-basic nitrogen atoms.

18. The radiation-sensitive recording material as claimed in claim 17, wherein the heteroaromatic radical is a 2-furyl or 3-furyl, 2-thienyl or 3-thienyl, 1-pyrrolyl, 2-pyrrolyl or 3-pyrrolyl, pyridyl, pyrimidinyl, pyrazinyl, benzofuryl, isobenzofuryl, benzo[b]thienyl, benzo[d][1,3]thiazolyl, benzo[c][1,2,5]oxadiazolyl (=benzofurazanyl) or indolyl radical.

19. The radiation-sensitive recording material as claimed in claim 14, wherein the proportion of acid-forming compound a) is about 0.25 to about 25% by weight based on the total weight of the nonvolatile constituents of the mixture.

20. The radiation-sensitive recording material as claimed in claim 19, wherein the proportion of acid forming compound a) is about 0.5 to about 10% by weight based on the total weight of the nonvolatile constituents of the mixture.

21. The radiation-sensitive recording material as claimed in claim 14, wherein the proportion of the compound b) is about 1 to about 50% by weight based on the total weight of the solids in the radiation-sensitive mixture.

22. The radiation-sensitive recording material as claimed in claim 21, wherein the proportion of the compound b) is preferably about 10 to about 40% by weight based on the total weight of the solids in the radiation-sensitive mixture.

23. The radiation-sensitive recording material as claimed in claim 14, wherein the proportion of the binder c) is about 1 to about 98.5% by weight based on the total weight of the radiation-sensitive mixture.

24. The radiation-sensitive recording material as claimed in claim 23, wherein the proportion of the binder c) is about 25 to about 90% by weight based on the total weight of the radiation-sensitive mixture.

25. The radiation-sensitive mixture as claimed in claim 24, wherein the proportion of the binder c) is about 50 to about 80% by weight, based on the total weight of the radiation-sensitive mixture.

26. The radiation-sensitive recording material as claimed in claim 14, wherein the mixture contains one or more additives selected from the group consisting of dyes, pigments, plasticizers, wetting agents, levelling agents, polyglycol and cellulose ethers.

* * * * *